(12) United States Patent
Bernardi et al.

(10) Patent No.: US 7,955,818 B2
(45) Date of Patent: Jun. 7, 2011

(54) METHOD FOR DETECTING THE FORMATION OF BIOFILMS

(75) Inventors: Thierry Bernardi, Perignat-les-Sarlieve (FR); Nicolas Bara, Paris (FR)

(73) Assignee: Thierry Bernardi (FR)

( * ) Notice: Subject to any disclaimer, the term of this patent is extended or adjusted under 35 U.S.C. 154(b) by 963 days.

(21) Appl. No.: 10/590,159

(22) PCT Filed: Feb. 23, 2005

(86) PCT No.: PCT/FR2005/000427
§ 371 (c)(1),
(2), (4) Date: Jun. 26, 2007

(87) PCT Pub. No.: WO2005/090944
PCT Pub. Date: Sep. 29, 2005

(65) Prior Publication Data
US 2008/0038769 A1       Feb. 14, 2008

(30) Foreign Application Priority Data

Feb. 23, 2004   (FR) ..................................... 04 01791
Jun. 28, 2004   (FR) ..................................... 04 07062

(51) Int. Cl.
*C12Q 1/04* (2006.01)
(52) U.S. Cl. ....................................... 435/34; 435/302.1
(58) Field of Classification Search .................... 435/34, 435/302.1
See application file for complete search history.

(56) References Cited

U.S. PATENT DOCUMENTS

| | | | |
|---|---|---|---|
| 3,635,678 A * | 1/1972 | Seitz et al. ....................... | 436/69 |
| 3,696,661 A | 10/1972 | Garabrant et al. | |
| 4,081,242 A | 3/1978 | Girolami | |
| 4,935,147 A * | 6/1990 | Ullman et al. ................. | 210/695 |
| 5,072,610 A | 12/1991 | Martinoli et al. | |
| 2002/0064866 A1 | 5/2002 | Tajima et al. | |
| 2002/0123077 A1* | 9/2002 | O'Toole et al. ................. | 435/7.2 |
| 2003/0012693 A1 | 1/2003 | Otillar et al. | |
| 2008/0213856 A1* | 9/2008 | Bara et al. .................. | 435/173.9 |

FOREIGN PATENT DOCUMENTS

| | | |
|---|---|---|
| FR | 2 555 316 A1 | 5/1985 |
| JP | 57-147492 A | 9/1982 |
| JP | 61-161436 A | 7/1986 |
| JP | 2003-210158 A | 7/2003 |
| WO | WO 01/86255 A1 * | 11/2001 |
| WO | WO 2004/111264 A1 * | 12/2004 |

OTHER PUBLICATIONS

Larson F. et al. Surface Adhesion Measurements in Aquatic Biofilms Using Magnetic Particle Induction: MagPI. Limnology and Oceanography: Methods vol. 7, 490-497, 2009.*

Filloux, A. et al., "Biofilm: Establishment and Organisation of a Bacterial Community," *Médecine Sciences*, Jan. 2003, vol. 19, No. 1, pp. 77-83 (English translation is attached).

Chicurel, M., "Slimebusters," *Nature*, Nov. 16, 2000, vol. 408, pp. 284-286.

Costerton, J. W. et al., "Bacterial Biofilmes: A Common Cause of Persistent Infections," *Science*, May 21, 1999, vol. 284 pp. 1318-1322.

* cited by examiner

*Primary Examiner* — Ralph Gitomer
(74) *Attorney, Agent, or Firm* — DLA Piper LLP (US)

(57) ABSTRACT

A process allowing measuring of viscosity of a culture medium of microorganisms including a) immersing at least one particle that is charged electrically, is magnetic or can be magnetized or covered with at least one magnetic or magnetizable layer in the culture, b) subjecting the culture to an electrical, magnetic or electromagnetic field in such a manner as to put the particle in motion, and c) optically detecting the degree of freedom of motion of the particle in the culture without a scanning microscope.

11 Claims, 8 Drawing Sheets

METHOD FOR DETECTING THE FORMATION OF BIOFILMS

RELATED APPLICATION

This is a §371 of International Application No. PCT/FR2005/000427, with an international filing date of Feb. 23, 2005 (WO 2005/090944 A1, published Sep. 29, 2005), which is based on French Patent Application Nos. 04/01791, filed Feb. 23, 2004, and 04/07062, filed Jun. 28, 2004.

TECHNICAL FIELD

This disclosure relates to the detection of the viscosity of a culture medium.

BACKGROUND

A microorganism is a living microscopic being such as bacteria, yeast and fungi, algae and protists. A microorganism can be unicellular or pluricellular. The larval stages of pluricellular organisms (metazoas) can also be the origin of biofilms.

The majority of microorganisms (pathogenic or non-pathogenic) have been studied up to the present in their "planktonic" form, free and isolated in a medium (cultivated in suspension or on a selective medium). In a natural medium outside of the laboratory the bacterial populations are found fixed on the support ("sessile" state) and developed in an organized community called a "biofilm". This bacterial community is generally enclosed in a matrix of exopolysaccharides (EPS) limiting exchanges with the surrounding medium (A. Filloux, I. Vallet. Biofilm: "Mise en place and organisation d'une communauté bactérienne" ("Placing and Organization of a Bacterial Community".) Medicine/Sciences 2003; 19: 77-83).

When a biofilm develops there is at first an adhesion of the bacteria on a support, then colonization of this support. When the bacteria multiply they rapidly form a film constituted of strata of cellular bodies secreting a sheath of exopolysaccharides that protects them against aggressions of the surrounding medium (Costerton et al. Bacterial Biofilms. Sciences 1999; 284-6). The kinetics of the formation of a biofilm can be subdivided into 5 stages:

Conditioning of the surface: The organic or mineral molecules present in the liquid phase will be absorbed on the surface in order to form a "conditioning film".

Adherence or reversible adhesion: The microorganisms present approach the surfaces by gravimetry, Brownian movements or by chemotaxis if they possess flagella. During the course of this first fixation stage, causing only purely physical phenomena and weak physico-chemical interactions to occur, the microorganisms can still be readily detached.

Adhesion: This slower stage caused interactions with stronger energy to occur as well as the microbial metabolism and the cellular appendages of the microorganism (flagellae, pili, etc.). Adhesion is an active and specific phenomenon. The first colonizers will attach themselves in an irreversible manner to the surface in particular by the synthesis of exopolysaccharides. This process is relatively slow and is a function of environmental factors and of the microorganisms present.

The maturation of the biofilm (development and colonization of the surface): After having adhered to a surface the bacteria multiply and regroup in order to form microcolonies surrounded by polymers. The matrix of polymers (or glycocalyx) will act like a "cement" and reinforce the association of the bacteria among themselves and with the surface in order to finally form a biofilm and attain a state of equilibrium. The biofilm generally develops in a tri-dimensional structure that constitutes a confinement site. This microenvironment will be the seat of numerous physiological and molecular modifications relative to the plantonic growth mode. The biofilm formed in this manner will occupy all the surface that is offered to it if the conditions permit it to do so. The maturation of the biofilm is generally correlated with the production of EPS even if certain species of microorganisms do not synthesize or if only few polymers can likewise adhere and form biofilms on the surfaces.

Detachment: Biofilms are structures in perpetual dynamic equilibrium and develop as a function of the support, of the microorganisms and of the environment this development can be expressed by the detachments of cells or of aggregates.

This release of cells into the liquid medium can allow as a consequence the contamination of the other surfaces and is in general the cause of numerous recurring diseases in a medical environment (source of resistances).

The nature of biofilms is very varied—some are very rich in ExoPolySaccharide (EPS) and others are principally constituted of bacterial bodies.

In human health, biofilms are responsible for infections that are becoming more and more difficult to suppress: in the entire ORL sphere (auditory conduit, nasal membrane, conjunctiva of the eye, etc.), on the teeth (appearance of tartar, caries, etc.), on the bronchi, the lungs (in patients afflicted with mucoviscidosis, etc.), in the urogenital tract, etc.

Furthermore, they are the origin of the majority of nosocomial pathologies (more than 10,000 deaths per year) by forming on catheters or implants (cardiac valves, artificial hips, urinary probes, etc.) (J. W. Costerton, P. Stewart and E. P. Greenberg, Bacterial Biofilms "A common cause of persistent infections". Science, vol. 284, pp. 1318-1322).

Biofilms are also present in refrigeration towers, responsible for infection by legionellas.

They also affect the agrofood industry on account of their implication in cases of food poisoning (formation during ruptures in the cold chain, development on cutting tools, crunching tools and on work surfaces).

Likewise, biofilms develop in pipes, causing, in particular, corrosion phenomena.

Biofilms also develop on the surface of immerged objects, such as, e.g., boat hulls, causing problems of fouling (dirtying of the surface of boat hulls due to the colonization of the hulls by various microorganisms).

It should be noted that bacteria are not alone in creating biofilms: Fungi, algae and Protozoa also organize into biofilms.

Biofilms are therefore omnipresent in numerous areas, presenting sanitary risks and causing relatively significant damage.

However, the development and the behavior of these biofilms remains poorly understood due to the fact of their complexity when being studied, although numerous methods for studying the development of biofilms have been implemented.

The methods for studying biofilms are still principally based on the colonization of pieces of glass or of plastic immerged in a culture medium contained in flasks under agitation in drying ovens in order to subsequently color them crystal violet or to observe them under a microscope.

There are other more complex detection methods such as, e.g., detections by Micro-balance with quartz crystal (Q-CMD, Quartz Crystal Microbalance with Dissipation Monitoring), detections by MTA (Mass Transport Analysis), by UFDR (Ultrasonic Frequency Domain Reflectometry), by PCR in situ (on functional gene Amo A), by FISH (hybridization in situ under fluorescence), by CLSM (Confocal Laser Scanning Microscopy), by PAS (Photo Acoustic Spectroscopy), etc.

Still other methods use particles/magnetic beads covered with lectin, or antibodies for isolating the bacteria responsible for the development of the biofilm, in order to then allow the characterization of these microorganisms by classic methods of immunoanalysis or by molecular biology (hybridization or PCR).

However, such methods have proven to be difficult to implement and remain relatively onerous. Furthermore, they do not allow a sufficiently probing teaching to be given about the behavior of the bacteria and therefore about the formation and development of biofilms. In fact, these methods do not allow the development of a biofilm to be followed, whether it is simply constituted of cellular bodies (Listeria type), EPS (exopolysaccharide) or an analogous matrix secreted by colonizing microorganisms (Pseudomonas type).

FR 2555316 discloses a process and an apparatus for determining the viscosity of a fluid medium, which process consists of immersing a conductive bead into the fluid medium, applying a rotating magnetic field substantially centered on the bead, which rotating field is such that the flow of the fluid in contact with the bead put in rotation remains laminar, and determining a magnitude connected with the couple exerted on the bead by virtue of the viscosity of the fluid medium. Thus, the bead, plunged in a viscous medium, undergoes a moment of braking proportional to the viscosity and assumes a rotation as a permanent speed whose period is also proportional to the viscosity of the liquid medium to be analyzed. The rotation of the bead can be visualized with the aid of diffraction discs obtained by lighting the bead with the aid of a laser beam along its axis of rotation.

However, such a process is only adapted for an implementation in a homogeneous viscous medium. A culture medium of bacteria is opalescent, cloudy and opaque. Therefore, this method does not allow a determination of the formation or lack of formation of biofilms in the culture medium.

JP 61-161436 discloses a method for measuring the viscosity of a non-Newtonian fluid based on the principle of magnetic attraction. The method consists of measuring the viscosity by means of the measurement of the displacement and the displacement rate of a magnetized bar under the effect of a magnetic field.

That method proposed allows the determination of the characteristics relative to the viscous fluid such as the viscosity. However, the method in question does not allow in any way a reproduction of the behavior of a microorganism such as a bacteria developing in the viscous fluid.

SUMMARY

We provide a process allowing measuring of viscosity of a culture medium of microorganisms including a) immersing at lest one particle that is charged electrically, is magnetic or can be magnetized or covered with at least one magnetic or magnetizable layer in the culture, b) subjecting the culture to an electrical, magnetic or electromagnetic field in such a manner as to put the particle in motion, and c) optically detecting the degree of freedom of motion of the particle in the culture without a scanning microscope.

We also provide an apparatus that allows measuring of viscosity of a culture of microorganisms including at least one culture reactor that receives the culture to perform detection of formation and development of biofilms, at least one particle that is electrically charged or is magnetic or magnetizable or covered with at least one magnetic or magnetizable layer, immersed in the culture, a generator that generates an electrical, magnetic or electromagnetic field, which field is applied to the particle, and an optical detector that detects motion of the particle, with the proviso that the optical detector is not a scanning microscope.

BRIEF DESCRIPTION OF THE DRAWINGS

The disclosure will be better understood with the aid of the scription, given below purely by way of explanation, of different selected, representative examples, with reference made to the attached figures.

DETAILED DESCRIPTION

Figure 1:
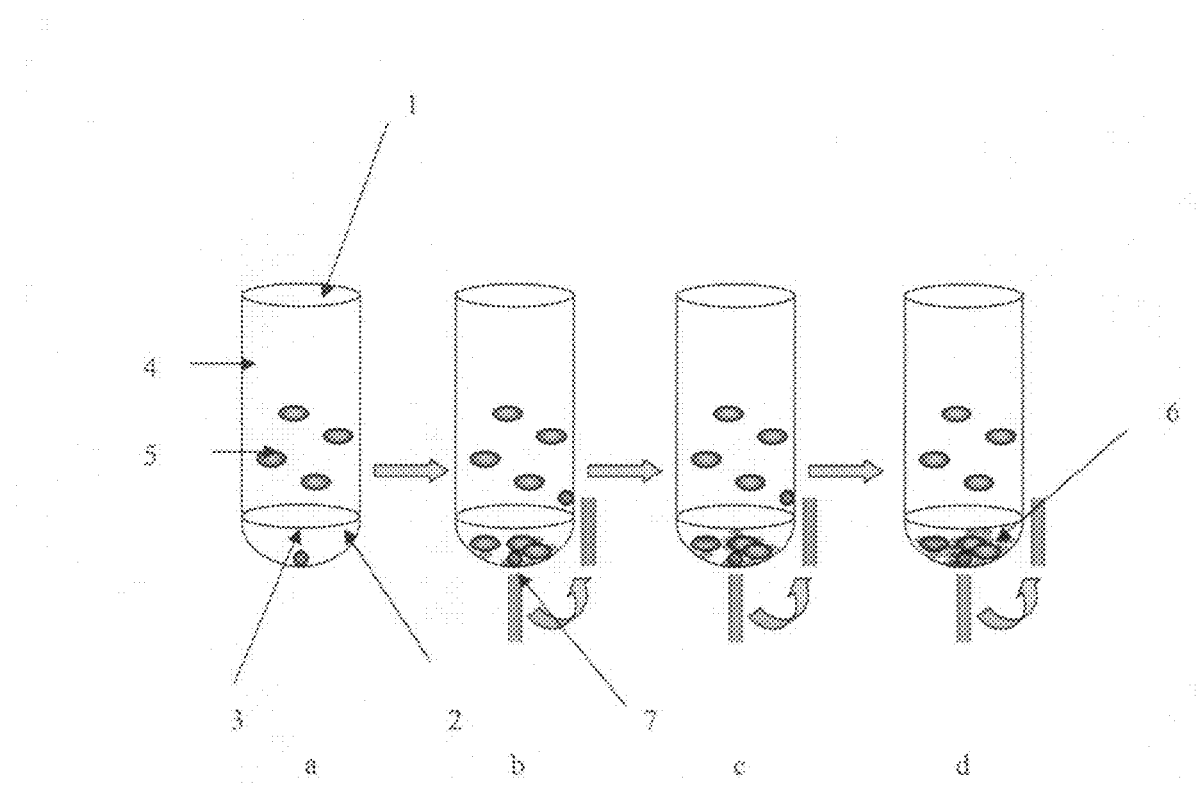
FIG. 1 illustrates the principle of the detection of the formation and of the development of a biofilm in a tube with a hemispherical bottom.

This disclosure relates to the area of the study of the development of a biofilm in a homogeneous or non-homogeneous culture medium. This biofilm hinders, as it develops, the movement of particles that can move in a magnetic, electrical or electromagnetic field such as particles that are charged electrically (by the presence of positive and/or negative ions) or magnetically or that are magnetic or magnetizable or covered by a magnetic or magnetizable layer.

In this connection, the term "viscosity" is to be understood as referring to the degree of liberty of the magnetizable particle in the biofilm. It will also be understood that this disclosure does not relate to measuring the viscosity of a medium as understood with the term "viscosity" in its common meaning, but rather the demonstration of the development of a microorganism by measuring the degree of liberty of one (or several) magnetizable particles whose movement is hindered or not hindered by a biofilm, which is significant itself of the presence or lacking presence of this microorganism in development.

Likewise, the expression "culture medium" is to be understood as any medium in which at least one microorganism can be present and developed. It therefore concerns a medium that can be natural or synthetic. Thus, e.g., water is included in this definition. The expression "culture medium" or the terms "medium" or "culture" can be used interchangeably by referring to this definition.

Thus, the terms "culture medium," "medium" or "culture" denote a microorganism and the medium in which it is found or possibly only the medium.

This disclosure relates to a process and an apparatus that allow the detection of the development of the viscosity of a culture medium, homogeneous or non-homogeneous, cloudy and/or opaque and to the use of this process and/or this apparatus in particular applications.

The term "non-homogeneous culture medium" should be understood in its broadest sense. In particular, a non-homogeneous culture medium comprises a limpid culture medium in which microorganism developed in suspension.

We therefore provide a process and apparatus that allow the modeling of the development of biofilms in a non-homogeneous, cloudy and opaque medium corresponding to the culture medium in which microorganisms develop to form such biofilms.

We also provide the modeling of the process of the colonization of a surface by microorganisms.

We further provide for the demonstration of the differences of viscosity in a in a non-homogenous medium and, consequently, allowing the modeling of the culture medium in different zones in accordance with the development of biofilms in each zone.

We still further provide a process and apparatus for the detection of the development of biofilms that is simple to implement, not very onerous and can be automated.

This is achieved in a process allowing the measuring of the viscosity of a culture medium of microorganisms comprising:
  a) the immersion of at least one particle that is charged electrically, magnetic or can be magnetized or covered with at least one magnetic or magnetizable layer in the culture,
  b) the subjection of the culture to an electrical, magnetic or electromagnetic field, preferably a magnetic field, in such a manner as to put the particle in motion,
  c) the optical detection of the degree of liberty of motion of the particle in the culture, preferably by optical measuring, which process does not use a scanning microscope.

Step b) includes subjecting the culture either to an electrical field or a magnetic field or an electromagnetic field, possibly applied by impulsion, or to a progressive augmentation of an electromagnetic field or to more complex variations of an electromagnetic field or to a combination of fields.

The progressive augmentation of the electromagnetic field is obtained according to a particular configuration by approaching a magnet along a rectilinear or sinusoidal trajectory or even according to an oscillatory motion that can have or not have a variable oscillation amplitude and a variable frequency. The more complex variations of the electromagnetic field are obtained by rotation or by combinations of movements of a magnetized bar in the proximity of the culture.

The electric, magnetic or electromagnetic field is advantageously generated by means for generating a field in motion.

The culture advantageously flows in a constant stream or in a discontinuous stream at given time intervals through an open reactor. The latter configuration is preferred to the extent that it allows an adequacy with the natural conditions of the development of a biofilm.

As concerns the particle, it can be either an electrically charged particle, a magnetic particle, arranged covered with at least one magnetic layer, a magnetizable particle or a particle covered with a magnetizable layer.

The magnetic particle can advantageously have a size approximately identical to the size of the microorganisms generating the biofilms.

It is also advantageously possible to use particles of different sizes and/or, also of advantage, of different colors. The smaller-sized particles are immobilized before the larger-sized particles during the development of a biofilm. It is thus possible to characterize more precisely the development of the biofilm or its degradation.

Likewise, according to an advantageous configuration, the particle generates a signal detectable by the apparatus for the optical detection of motion. The signal can be detected either in an autonomous manner (advantageously by radioactivity) or by re-emission of energy transmitted in continuous or discontinuous streams (advantageously luminous transmission of energy by laser beam and re-emission of fluorescence).

The particle is advantageously of the fluorescent, phosphorescent, radioactive or chemo-luminescent type.

Step c) may include lighting the particle with a light source and detecting the motion of the particle in the culture.

In order to do this, this particle can advantageously be fluorescent.

The particle 3 may be configured in such a manner that it is in a stable position at rest (in the absence of a field) in reactor 1. The particle can advantageously be a particle, e.g., in the form of a hockey puck, with an asymmetric geometry with a plane face, etc.

Furthermore, the process may include performing a measuring of the viscosity of the culture according to the process as previously described at a time t=0 corresponding to the seeding of the culture and at least one measuring at a time t of the viscosity of the culture according to the process as previously described, as well as comparing these measurements at t0 and t.

The process allows measuring of the viscosity of a culture of homogeneous or non-homogenous microorganisms, preferably non-homogeneous ones.

We further provide an apparatus that allows the realization of the process as previously described.

Thus, we provide an apparatus that allows measuring the viscosity of a culture of homogeneous or non-homogenous microorganisms, comprising:
  at least one culture reactor for receiving the culture to perform the detection of the formation and development of biofilms,
  at least one particle that is electrically charged or is magnetic or magnetizable or covered with at least one magnetic or magnetizable layer, immersed in the culture,
  means for generating an electrical, magnetic or electromagnetic field, preferably a magnetic field, which field is applied to the particle in such a manner as to put it in motion, and
  an apparatus for the optical detection of the motion of the particle, other than a scanning microscope.

The term "culture reactor" denotes either an enclosure with at least one closed end of the tube type, well, etc. (closed reactor), or an enclosure with two openings for allowing the culture to flow through the enclosure (open reactor).

Thus, the reactor may have a closed end in such a manner as to form a flat bottom.

In order to have a stable position at the bottom of the tube when the particle is at rest, that is to say, when no field is generated, the reactor bottom can have one or several cavities or grooves for receiving the particle or particles.

The reactor may have a closed end in such a manner as to form a hemispherical bottom.

The reactor can have two open ends. In this configuration, the reactor can be configured in such a manner as to allow the culture to flow in a constant stream or in a discontinuous stream at given time intervals.

As concerns the particle, it is advantageously either a particle that is electrically charged (by the presence of positive and/or negative ions), or a magnetic particle, or a particle covered with at least one magnetic layer, or a magnetizable particle, or a particle covered with at least one magnetizable layer.

The magnetic particle advantageously has a size approximately identical to the size of the microorganisms that generate biofilms.

It is advantageously possible to use particles with different sizes and, also advantageously, of different colors. The smaller-sized particles are immobilized before the larger-sized particles during the development of a biofilm. It is thus possible to characterize more precisely the development of the biofilm or its degradation.

Likewise, according to an advantageous configuration, the particle generates a signal detectable by the apparatus for the optical detection of motion. The particle is advantageously of the fluorescent, phosphorescent, radioactive or chemo-luminescent type.

Concerning the apparatus for the optical detection of motion, it comprises a light source transmitting in the direction of the particle, and optical detection means allowing detection of the motion of the particle in the culture. The term "optical detection means" denotes any usable detection means. Macroscopic optical means may be concerned. The motion of the particle can be visualized directly with the naked eye.

Within the scope of such detection, the illuminated particle can include a fluorescent particle or a particle that is black or at least opaque.

Particles of different colors, sizes, densities, shapes, geometries, physico-chemical constitutions, surface states can be used with advantage to multiply the criteria for the characterization of the development of a biofilm.

Chemical groupings to be tested can be coupled with advantage to the surface of the particle and the anti-adhesion properties of these chemical groupings (mobile particles) can be tested.

Molecules allowing the characterization of certain categories of microorganisms can be advantageously coupled to the surface of the particles and the adhesion of these categories of microorganisms (immobilized particles) tested.

The particle can be directly configured to rest in a stable position at rest in the flat bottom of this reactor. The particle can advantageously be a particle, e.g., in the form of a hockey puck, with an asymmetric geometry with a plane face, etc.

Furthermore, the apparatus can advantageously comprise measuring means for measuring the viscosity of the culture at given time intervals and comparison means allowing the measurements obtained to be compared.

It is possible in this manner to test the hindrance to the displacement of the particle due to the presence of colonizing microorganisms or of exopolysaccharides or of matrix secreted by the microorganisms in which the particle is encased at different times.

The general principle for detecting the formation and development of a biofilm in a culture containing microorganisms takes place as follows.

One or more particles or beads that are charged electrically, magnetic, magnetizable or covered with a magnetic or magnetizable layer is/are placed in the culture. The composition of the particles can vary on the condition that it is compatible with a reactivity in an electric, magnetic or electromagnetic field. To simplify the following description, the particles will only be described in terms of beads.

The beads are found incorporated little by little in the matrix secreted by the microorganisms until a complete immobilization.

In the biological process of the formation of the biofilm, the microorganisms are immobilized and surrounded in the matrix. They are then concealed, protected from aggressions from the outside medium, whence the origin of observed resistances to antibiotics (nosocomial pathologies). The beads allow this immobilization to be mimicked.

To mimic this immobilization, a field generator is applied to these beads. Thus, in the mediums in which no biofilm has developed the beads react to the approach of the generator and move, in general, toward the field generator and possibly follow the movement of the generator. On the other hand, if the particles are surrounded in the matrix of the biofilm their movement will be checked and even prevented according to the degree of the formation of the biofilm.

Therefore, the method resides in the exploitation of the behavior of beads that can be put in motion under the effect of electrical, magnetic or electromagnetic fields. If the behavior of these beads is hindered by the presence of the matrix in the biofilm, it is then possible to detect and visualize their degree of mobility (mobile, semi-mobile, immobile) and consequently to visualize the development of the biofilm.

Furthermore, the method allows for the differentiation of the beads that can be put in motion under the effect of a field and those whose movements are hindered by the presence of the matrix secreted by the microorganisms.

Detection of the motion of beads in the biofilm is carried out by optical measuring, either by direct illumination or by indirect illumination. In this latter instance, the beads are advantageously fluorescent.

The bacterial body will be mimicked more or less precisely and the development of the biofilm characterized with new criteria as a function of the selected format of the beads (geometry, size, density).

The dynamic development of the matrix constituting the biofilm can be followed as a function of the presentation frequency of the field generator and as a function of the field force. Likewise, once a biofilm has been constituted, its degradation can be followed under the effect of a particular treatment.

It is then possible to analyze the constitution of the matrix with biochemical tests.

Likewise, the following of the immobilization of the bead by the matrix constituting the biofilm allows the following, by analogy, of the process of the burying of bacteria in the matrix that they secrete.

To test the development of the biofilm at the bottom of a tube, the detection is conducted with particles that are sufficiently dense to settle on the bottom of the tube. Inversely, the detection is conducted with particles that are not very dense so that they float at the surface of the culture medium to be able to study the development of biofilm on the surface (air/liquid interface).

Moreover, by using the density of the particles, a series of detections can be conducted at solid/liquid, liquid/liquid, liquid/gas interfaces.

The detections can also use particles with different sizes that can also be, e.g., differentiated by different colors.

Examples of the method will now be described. In the examples, the microorganisms described are bacteria. It is understood that the following description is applicable to any other microorganism for which the development of its biofilm is to be studied. However, the size of the beads is advantageously adapted to the size of the microorganisms studied if one wishes to model the behavior of the microorganisms in the biofilm formed.

FIGS. 1 to 8 illustrate the principle of the detection of the formation of a biofilm in different tube geometries that receive a culture containing the bacteria to be studied.

Figure 2:
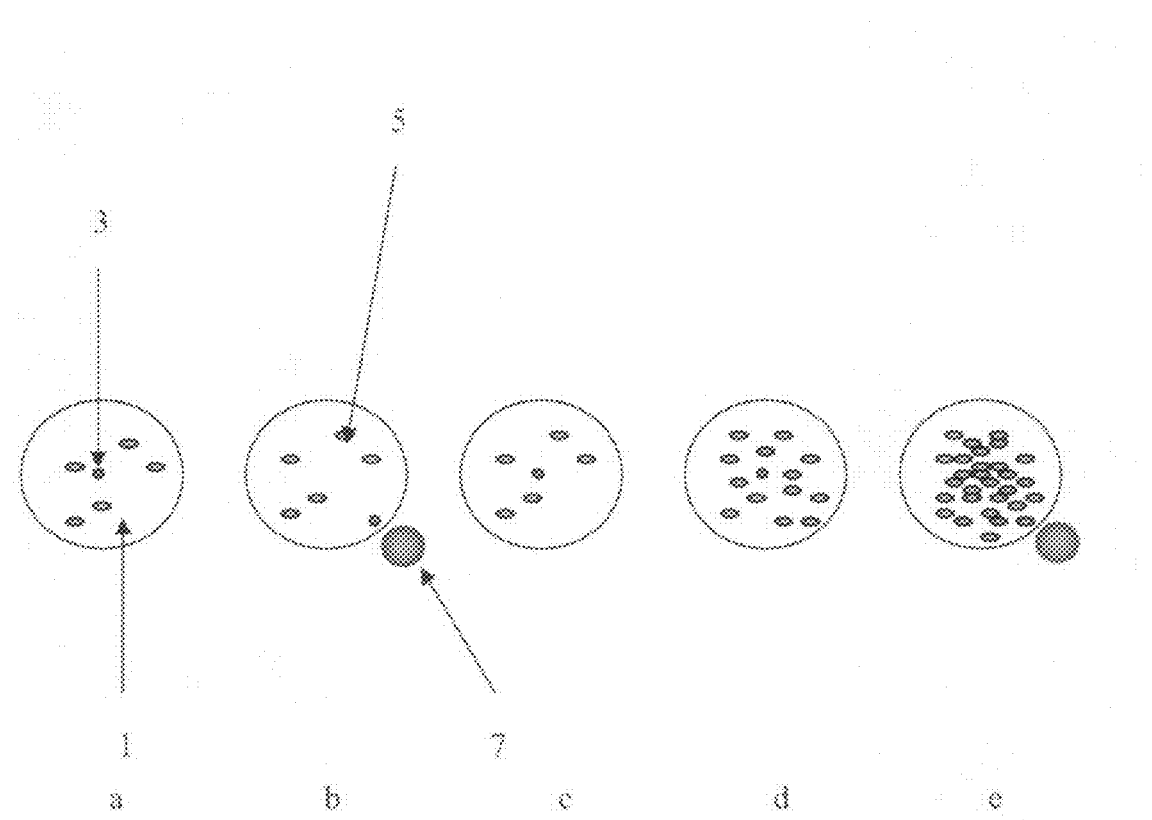
FIG. 2 is a top view showing the principle of the detection of the formation of a biofilm on the bottom of a tube with a hemispherical bottom (or of tubes other than with a flat bottom)

FIGS. 1 and 2 illustrate in particular the principle of the detection of the formation and of the development of a biofilm in a reactor 1 of the tube type with a hemispherical bottom 2. FIG. 1 is an illustration in section and FIG. 2 is a top view.

For example, an experiment can be conducted on a plate having 96 tubes (or wells) containing 200 μl. In the present example, a bead 3 is placed at the bottom of each tube 1. Of course, the process is not limited necessarily to a single bead. A culture medium 4 is then added into each tube 1, which medium is then seeded with a bacterial strain 5 that can develop into a biofilm 6 under standardized culture conditions (temperature, oxygenation, pH, etc.).

A magnet 7 positioned under tube 1 and more particularly under bead 3 is moved at regular time intervals so as to rise up regularly along the wall of tube 1.

When bead 3 does not encounter any obstacle in its motion or is not sufficiently hindered in the matrix secreted by bacteria 5 constituting biofilm 6, bead 3 follows the motion of magnet 7 (FIGS. 1b and 1c or 2b and 2c). When the magnet is removed, the bead is no longer subjected to its field and can return to its initial position. On the other hand, when the formation of biofilm 6 is such that the motion of bead 3 is hindered or even prevented, bead 3 remains immobile at the bottom of tube 1 (FIG. 1d or 2d). This state thus expresses a development of the extracellular matrix constituting biofilm 6 in tube 1, such that the matrix surrounds bead 1 in the same manner as it surrounds bacteria 5.

In this example, the magnet is manipulated in such a manner as to move bead 3 along the wall of tube 1. However, it can be advantageous to manipulate the magnet in the direction of bead 3 or inversely to manipulate the tube toward the magnet in such a manner as to move bead 3 according to another trajectory than the wall of tube 1.

An optical apparatus advantageously allows the degree of liberty of the bead to be visualized (not shown). The apparatus comprises a light source emitting in the direction of bead 3 and comprises detection means allowing movement of bead 3 in culture 4 to be detected.

When tube 3 is transparent, the light source is located under the tube in such a manner as to emit the light beam directly toward magnetic bead 3. The detection means are then arranged above tube 3. Thus, detection of the motion of bead 3 is carried out following the movement of the dark spot corresponding to bead 3.

When tube 1 is of an opaque material such as, e.g., metal, the light source is arranged above the tube in such a manner as to emit the light beam through culture 4 towards magnetic bead 3. As above, these detection means are arranged above the tube. In this configuration, beads 3 are advantageously constituted of a fluorescent material. Thus, when beads 3 are illuminated via the light source, their movement is detected by the detection means by following the movement of the fluorescent spot corresponding to bead 3.

Figure 3:
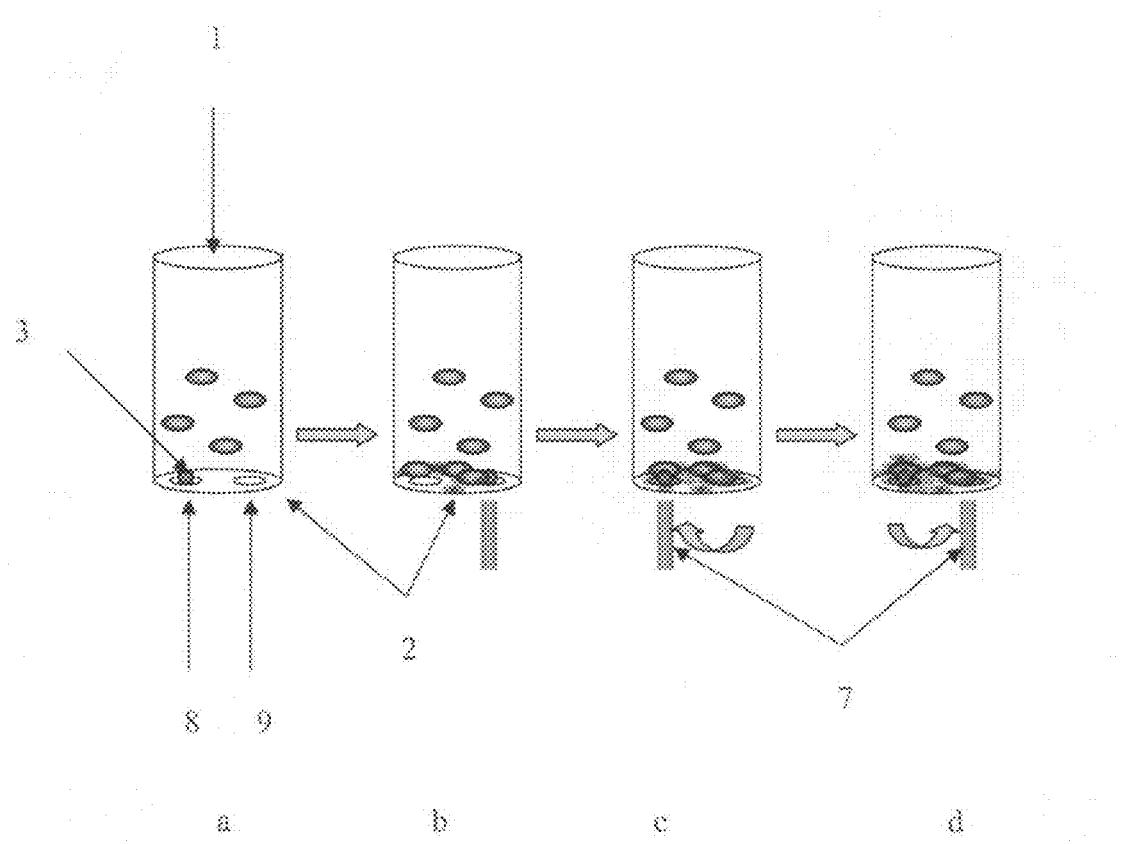
FIG. 3 represents the principle of the detection of the formation and of the development of a biofilm in a tube with a flat bottom.

FIG. 3 illustrates another aspect: detection of the formation of biofilm 6 in a reactor 1 of the type of a tube with a flat bottom 2.

Bottom 2 of tube 1 is advantageously provided with two adjacent cavities 8, 9. A bead 3 is placed initially in one of the cavities 8. Magnet 7 is then arranged in contact with the other cavity 9. When bead 3 is not hindered in its movement by biofilm 6, it glides from cavity 8 to adjacent cavity 9 (FIG. 3b). Magnet 7 is then moved under first cavity 8 (FIG. 3c). Bead 3 glides toward first cavity 8 under the attraction of magnet 7 with its motion still not being prevented or at least not sufficiently hindered. The test is repeated at regular intervals until observation of the total or partial immobilization of the beads 3 as illustrated in FIG. 3d: when magnet 7 is moved under the second cavity 9, bead 3 stuck in biofilm 6 can no longer pass in response to the attraction of magnet 7 into second cavity 9 due to the fact of the hindering of its motion in biofilm 6.

The tube bottom may not have cavities for receiving the magnetic bead or beads. To this end, the magnetic bead is configured to be able to maintain itself in a stable position at the bottom of tube 1.

Figure 4:
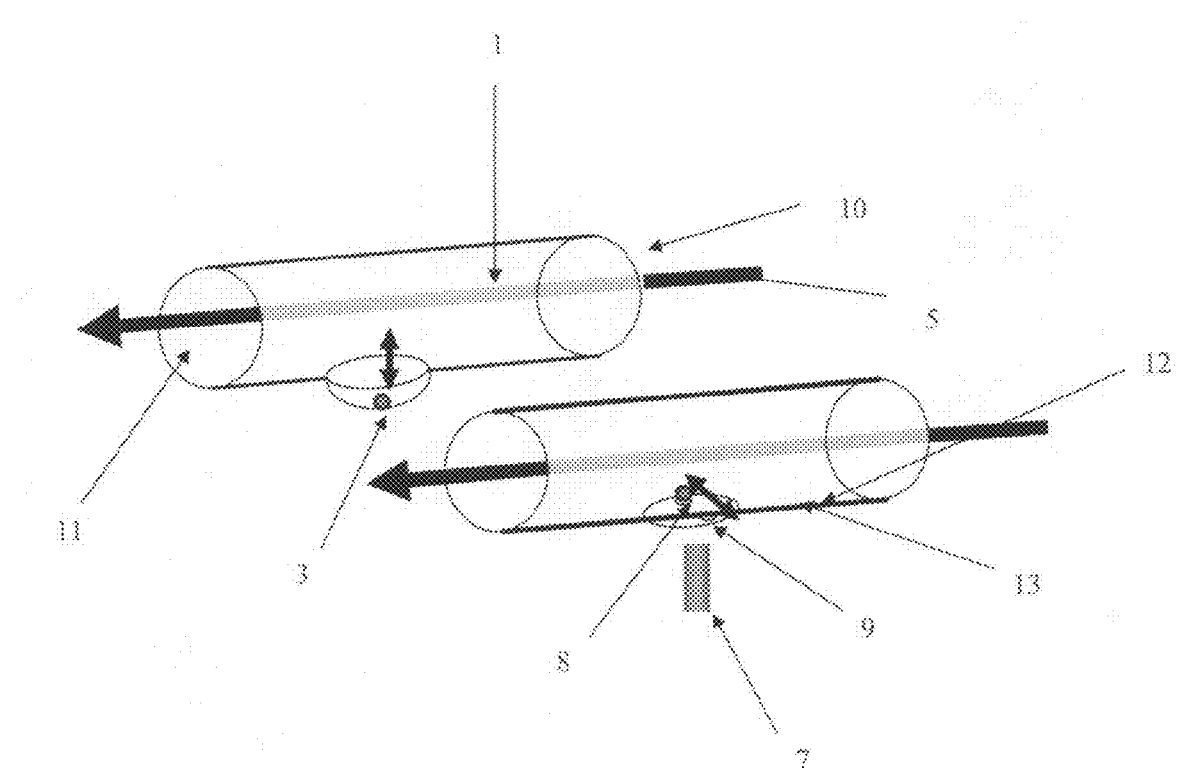
FIG. 4 represents the principle of the detection of the formation and of the development of a biofilm in a tube with open ends.

FIG. 4 illustrates another aspect using a reactor 1 of the tube type with two open ends 10, 11. Tube 1 is then configured to permit a continuous stream of culture medium 5.

As in the example of the tube with a flat bottom, inner surface 12 of wall 13 of tube 1 advantageously has cavities 8, 9 for receiving bead or beads 3. According to the same principle as the one previously described, magnet 7 is presented in such a manner as to put beads 3 in motion in such a manner that they pass from one cavity to the other.

In the instance in which no cavity is formed in inner surface 12 of wall 13 of tube 1, the principle is similar to the one described for the tube with a hemispherical bottom: magnet 7 is presented and moved in such a manner as to bring the beads up on inner face 12 of wall 13 of tube 1.

The beads encased in biofilm 6 can be subsequently recovered by a magnet being immersed into the culture. In this manner, a fragment of the biofilm is taken for tests of physical characterization (viscosity of the matrix, etc.), chemical and biochemical characterization (constituent elements of the matrix, etc.), and biological characterization (microorganisms constituting the matrix in a state of latency, inactivity, dead bodies, etc.).

Figure 5:
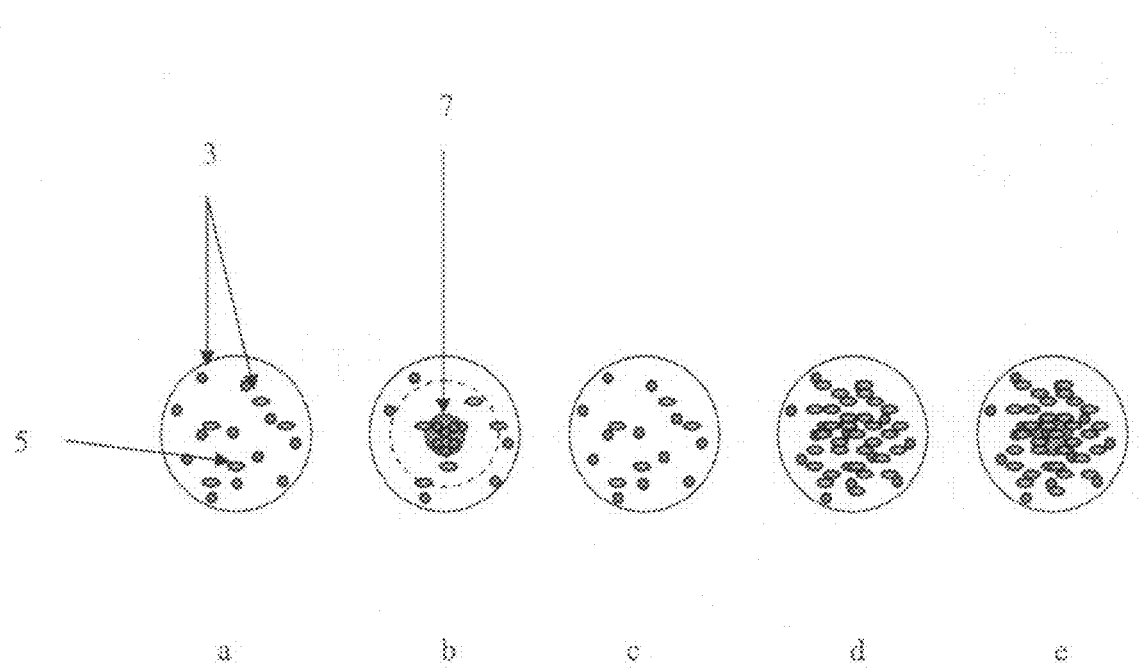
FIG. 5 represents another illustration of the principle of the detection of the formation and of the development of a biofilm in a reactor of the type of a tube with a flat bottom.

FIG. 5 is another illustration of the principle of the detection of the formation and development of the biofilm in a reactor 1 of the tube type with a flat bottom 2. This illustration is a plane view from the top of the tube.

Beads 3 are placed at the bottom of each tube 1. A culture medium 4 is then added into each of the tubes (FIG. 5a), which medium is then seeded with a bacteria strain 5 that can develop into biofilm 6 (FIGS. 5b to 5e) under standardized culture conditions (temperature, oxygenation, pH, etc.).

A magnet 7 is positioned at regular time intervals under tube 1 (FIGS. 5b and 5e). When beads 3 do not encounter an obstacle in their motion or are not sufficiently hindered in the matrix secreted by bacteria 5 and constituting biofilm 6, they are attracted in the direction of magnet 7 (FIG. 5b). Beads 3 attracted around magnet 7 free a zone "without beads" or "clear zone" that is simple to detect, particularly visually. When the formation of biofilm 6 is such that the motion of beads 3 is hindered or even prevented, these beads 3 remain immobile at the bottom of tube 1 (FIGS. 5d and 5e). This state then expresses a development of the extracellular matrix constituting biofilm 6 in tube 1 such that the matrix surrounds magnetic bead 1 in the same manner as it surrounds bacteria 5.

Figure 6:
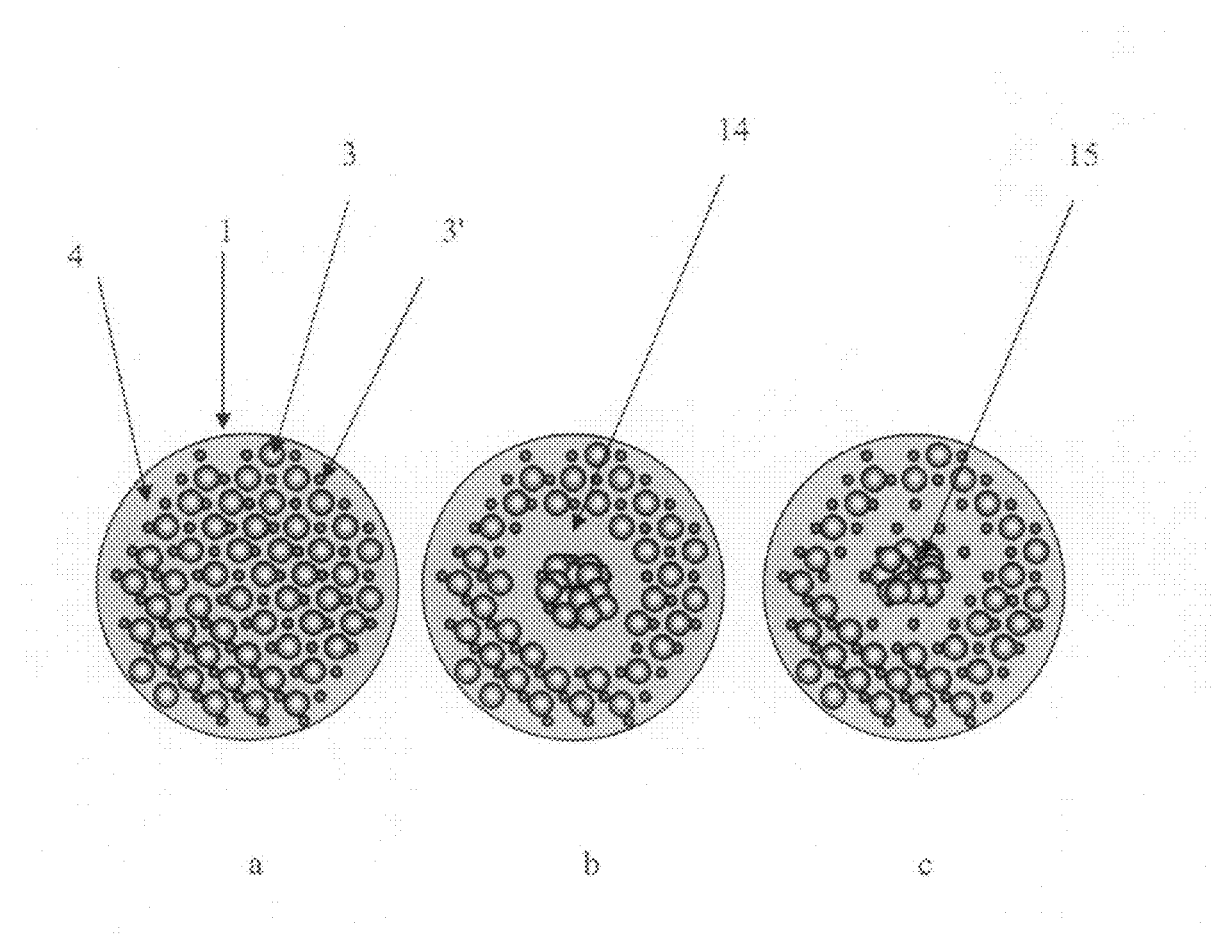
FIG. 6 represents another aspect of the disclosure shown in FIG. 5.

FIG. 6 illustrates another aspect of the disclosure shown in FIG. 5.

Figure 7:
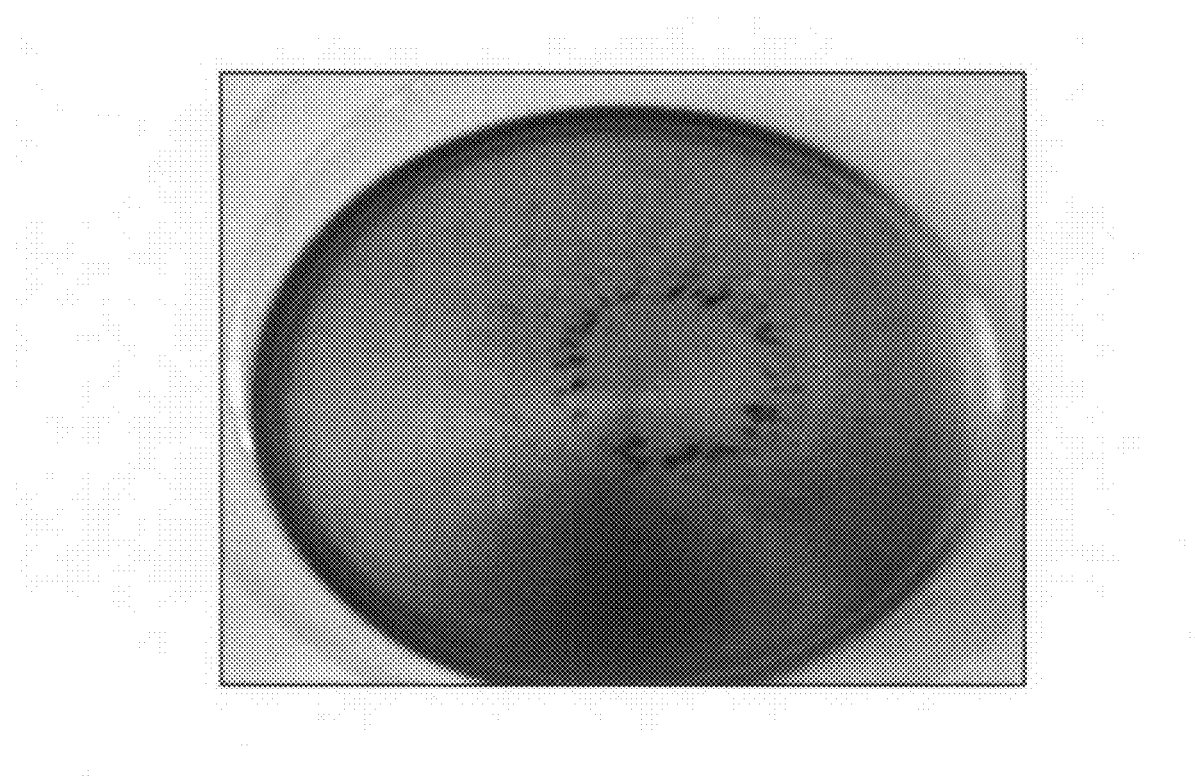
FIG. 7 represents a particular application as it is described in FIG. 5.

Petri dishes 1 containing a liquid culture medium 4 are seeded with bacteria 5, and magnetic beads 3 and 3' of different sizes are placed in each dish 1 (FIG. 7). The culture conditions are standardized (temperature, oxygenation, pH, etc.) to allow development of bacteria and therefore development of biofilm 6.

Magnet 7 is positioned under the Petri dish at regular time intervals. When bead 3 does not encounter an obstacle in its motion or is not sufficiently hindered in the matrix secreted by bacteria 5 and constituting biofilm 6, magnetic beads 3 are attracted in the direction of magnet 7. A clear zone 14 then develops between the outer limit of the influence zone of the magnetic field lines 9 that attract the beads and the aggregate of the beads 15. When the formation of biofilm 6 is such that the motion of beads 3 is hindered or even prevented, these beads 3 remain immobile in dish 1. However, due to the fact of the difference in size of the beads their movement is a function of their size and the density of the biofilm. As the biofilm develops, the small beads will have their movement inhibited by the biofilm first, then, with a supplementary development of the biofilm the large beads will be stopped in their turn.

FIG. 7 illustrates a particular application as it is described in FIG. 5 or in FIG. 6 with the beads placed on a surface covered with a product containing an anti-microbial agent such as, e.g., an anti-fouling agent. This surface can be of any material, in particular of metal. When a magnet is approaches the surface, the beads are attracted by the force lines of the magnet, that then constitute a bead density zone larger than on the rest of the surface. This application is advantageous when it is desired to measure the effectiveness of an anti-fouling product applied on a metallic surface.

It can be more interesting to vary the intensity of the magnetic field, e.g., by rotating a magnetized bar under the surface to be tested.

Figure 8:
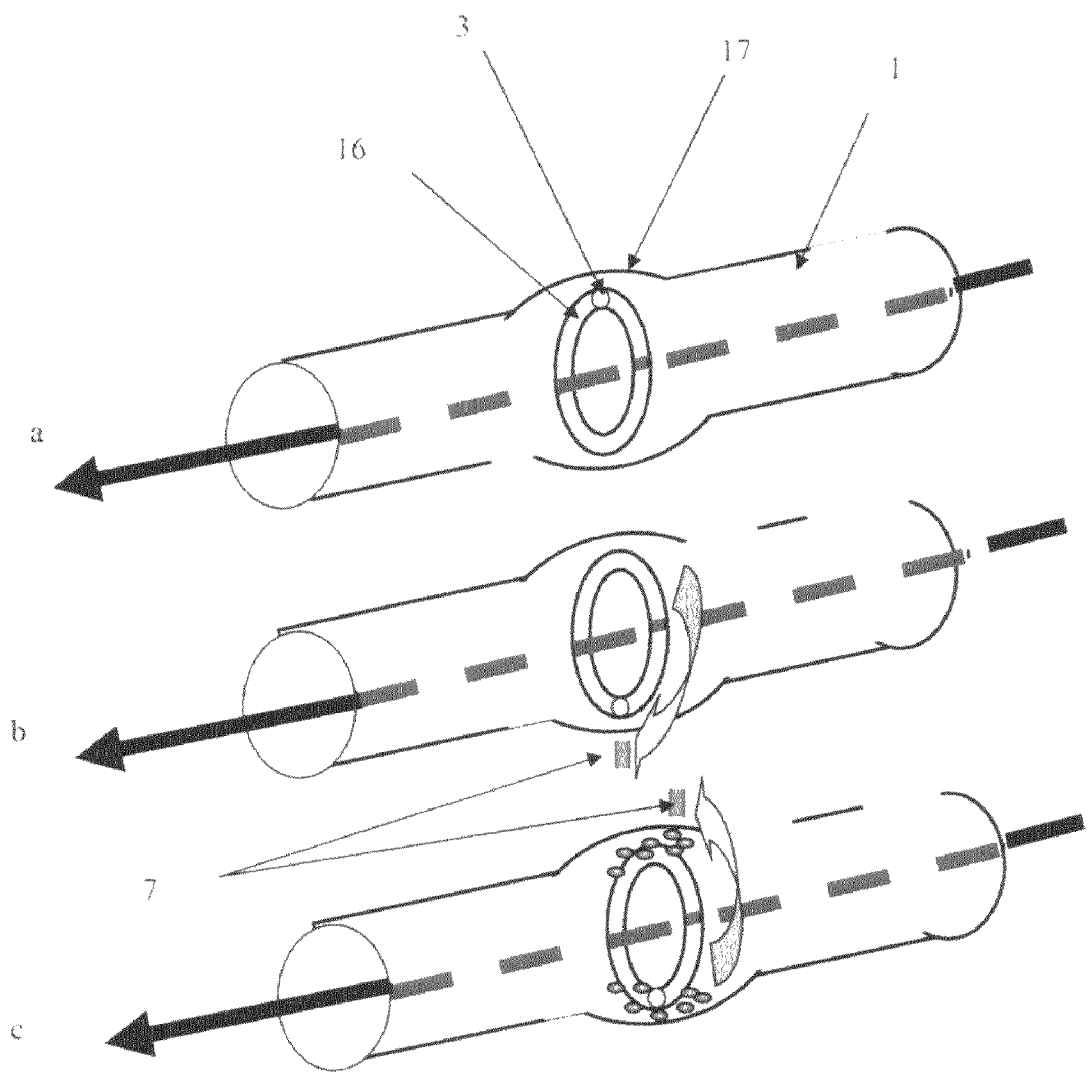
FIG. 8 represents a particular application in the area of the surveillance of the contamination of pipes, particularly the surveillance of the contamination of valves.

FIG. 8 illustrates a particular application in the area of the surveillance of the contamination of pipes, particularly in the surveillance of the contamination of valves.

To model the development of biofilm on a support subjected to a liquid stream (pipes 1), it is possible to use an apparatus with an annulus 16 held in a bulge of a tube 17. A magnetizable particle 4 is enclosed at a point of annulus 2. This annulus can be rotated under the action of a magnetic field (FIG. 8*b* or 8*c*).

If a biofilm develops in the apparatus the motion of the annulus is hindered.

This apparatus models a valve, the site in pipes where biofilms develop most readily.

This disclosure is described above by way of example. It is understood that one skilled in the art is capable of realizing different variants without departing from the scope of the appended claims.

The invention claimed is:

1. A method for detecting formation and development of a microorganism biofilm on a surface in a liquid medium comprising:
   a) introducing into said medium at least one particle that is charged electrically, magnetic or magnetizable or covered with at least one magnetic or magnetizable layer,
   b) keeping the medium in conditions that permit development of a biofilm by said microorganism on said surface, said at least one particle resting on said surface, and
   c) detecting formation of a biofilm on said surface by application of an electric, magnetic or electromagnetic field to set into motion said at least one particle, the formation of a biofilm being detected when the motion of said at least one particle on said surface is slowed down or prevented due to formation of the biofilm.

2. The method according to claim 1, wherein step c) comprises subjecting said at least one particle to an electric, magnetic or electromagnetic field that is applied by impulsion.

3. The process according to claim 1, wherein step c) comprises subjecting said at least one particle to a progressive augmentation of an electric, magnetic or electromagnetic field.

4. The method according to claim 1, wherein said medium flows in a constant stream through an open reactor.

5. The method according to claim 1, wherein the medium flows at a discontinuous stream through an open reactor at given time intervals.

6. The method according to claim 1, wherein in step c) the at least one particle is lighted with a light source and motion of the lighted particle is detected.

7. The method according to claim 1, wherein the at least one particle generates a signal.

8. The method according to claim 1, wherein the at least one particle is fluorescent, phosphorescent, radioactive or chemo-luminescent.

9. The method according to claim 1,
   wherein several particles are introduced into the medium in step a), and
   wherein formation of a biofilm on said surface is detected in step c) by applying an electric, magnetic or electromagnetic field to set into motion said particles, formation of a biofilm being detected when the particles cannot be brought together on said surface by the electric, magnetic or electromagnetic field.

10. The method according to claim 1, wherein when particles can be grouped together and detection of the grouping is visual.

11. The method according to claim 1, wherein said medium is homogeneous or non-homogeneous.

* * * * *